United States Patent [19]

Cutroneo

[11] Patent Number: 5,798,334
[45] Date of Patent: Aug. 25, 1998

[54] PHARMACEUTICAL COMPOSITIONS FOR SCARLESS TISSUE REPAIR AND REGENERATION AND METHODS RELATED THERETO

[75] Inventor: Kenneth R. Cutroneo, Burlington, Vt.

[73] Assignee: Colla-Gene, Inc., Burlington, Vt.

[21] Appl. No.: 535,672

[22] Filed: Sep. 28, 1995

[51] Int. Cl.$^6$ .................... A61K 38/18; C07K 14/475; C07K 14/495
[52] U.S. Cl. .................................. 514/12; 514/21
[58] Field of Search .......................... 514/12, 21

[56] References Cited

PUBLICATIONS

Meisler, et al., "Dexamethasone Abrogates the Fibrogenic Effect of Transforming Growth Factor–(beta) in Rat Granuloma and Granulation Tissue Fibroblasts," The Society for Investigative Dermatology, Inc., 108:285–289 (1977).

Ritzenthaler et al., Regulation of the $\alpha 1$ (I) collagen promoter via a transforming growth factor–$\beta$ activation element. J. Biol. Chem. 268:12625–16631 (1993).

Jimenez et al., Functional analysis of human $\alpha 1$ (I) procollagen gene promoter, J. Biol. Chem. 269:12684–12691 (1998).

Rossi et al, A nuclear factor 1 binding site mediates the transcriptional activation of a type 1 collagen promoter by transforming growth factor $\beta$. Cell 52:405–414 (1988).

Inagaki et al., Transforming growth factor $\beta$ stimulates $\alpha 2$ (I) collagen gene expression through a cis–acting lement that contains an Sp1–binding site. J. Biol. Chem. 269:14828–14834 (1994).

Ritzenthaler et al., Transforming–growth–factor–$\beta$ activation elements in the distal promoter regions of the rat $\alpha 1$ type I collagen gene, Biochem. J. 280:157–162 (1991).

Newman et al., Glucocorticoids selectively decrease the synthesis of hydroxylated collagen peptides, Mol. Pharmacol. 14:185–198 (1978).

Lichtler et al., Isolation and characterization of the rat $\alpha(1)$ collagen promoter, J. Biol. Chem 264:3072–3077 (1989).

"Current Protocols in Molecular Biology" (vol. 1, p. 1.7.6).

Chen et al., High–efficiency transformation of mammalian cells by plasmid DNA, Mol. Cell Biol. 7:2745–2752 (1987).

Gorman et al., Recombinant genomes which express chloramphenicol acetyltransferase in mammalian cells. Mol. Cell Biol. 2:1044–1051 (1982).

Southern et al., Transformation of mammalian cells to antibiotic resistance with a bacterial gene under control of the SV40 early region promoter, J. Mol. Appl. Genet. 1:327–341 (1982).

Neumann et al., A novel rapid way for chloramphenicol acetyltransferase gene expression, BioTechiniques, 5:444–447 (1987).

Lowry et al., Protein measurement with the folin phenol reagent, J. Biol. Chem. 193:265–275 (1951).

Andrews et al., A rapid micropreparation technique for extraction of DNA–binding proteins from limiting numbers of mammalian cells, Nucleic Acid Res. 19:2499 (1991).

Cutroneo et al., anti–inflammatory steroids and collagen metabolism: Glucocorticoid–mediated alterations of prolyl hydroxylase activity and collagen synthesis, Mol. Pharmacol. 11:632–639 (1975).

Martens et al., Gut, 33(12) pp. 1664–1670 (1992). Abstract.

Amento and Beck, Ciba Foundation Symposium, (157) discussion 123–9, pp. 115–123 (1991). Abstract.

Beck et al., J. Clin. Invest. 92(6) 2841–9 (1993).

"Dexamethasone Abrogates the Fibrogenic Effect of Transforming Growth Factor–$\beta$ in Rat Granuloma and Granulation Tissue Fibroblasts," N. Meisler et al., in J. Invest. Dermatol., 108:285–289, 1997.

*Primary Examiner*—Cecilia J. Tsang
*Assistant Examiner*—P. Lynn Touzeau
*Attorney, Agent, or Firm*—Hale and Dorr LLP

[57] ABSTRACT

The invention relates to a pharmaceutical composition for normalizing the fibrogenic effect of an agonist which comprises an effective amount of an agonist to stimulate normal collagen synthesis together with an effective amount of an antagonist to reduce the agonist–mediated increase of collagen synthesis and collagen gene expression, together with a pharmaceutically acceptable carrier. The invention also relates to a method of normalizing the fibrogenic effect of an agonist with said composition.

9 Claims, 3 Drawing Sheets

1

PHARMACEUTICAL COMPOSITIONS FOR SCARLESS TISSUE REPAIR AND REGENERATION AND METHODS RELATED THERETO

BACKGROUND OF THE INVENTION

This invention relates to pharmaceutical compositions and methods related thereto for scarless tissue repair and regeneration in which the fibrogenic effect of an agonist is partially blocked by an effective amount of antagonist to normalize collagen synthesis. The antagonist reduces the agonist-mediated increase of collagen synthesis and collagen gene expression, thereby reducing the amount of fibrotic growth that causes scarring.

The wound healing process naturally occurs in response to injury and is brought about by the interplay of several systems with the ultimate objective of self-preservation. The systems which are thought to be important to the wound healing process and which are part of the reserve potential of the tissues include the inflammatory response, angiogenesis, collagen synthesis and deposition, and epithelization. Although tissue repair and regeneration usually occur without intervention, acceleration of collagen synthesis by an agonist may actually promote the replacement of functional healthy tissues with non-functional scar tissues. The invention described herein specifically promotes scarless tissue repair by limiting excessive collagen synthesis and deposition, thereby decreasing the risk of excessive scar formation.

This therapeutic approach may be applicable to any wound, accidental as well as surgical, or injury repair disorder. It is especially applicable to surgical incisions, such as those encountered in plastic surgery, in which the formation of a scar is an undesirable outcome. The approach may also be of value in treating burn victims, for whom scar formation is the usual outcome of their healing process.

Growth factors promote wound healing by increasing the expression of a wide variety of genes, including collagen, as well as by recruiting cells to the injury site. It has previously been demonstrated that Transforming Growth Factor-Beta (TGF-$\beta$) treatment results in the induction of the expression of pro$\alpha$1(I) collagen gene.[1-5] On the other hand, inflammatory steroids, such as dexamethasone, restrict or abate the wound healing process by selectively decreasing expression of collagen synthesis.[6]

SUMMARY OF THE INVENTION

The object of the invention is to provide a pharmaceutical composition and a method that combine an agonist to stimulate wound healing with an antagonist to reduce the agonist-mediated increase of collagen synthesis and collagen gene expression. The agonist may be a fibrotic growth factor. The antagonist may be a hormone, a vitamin, a vitamin derivative, or a drug.

Growth factors activate the serine threonine kinase signal transduction pathway, as well as other signal transduction pathways. It has been found that the fibrotic growth factor TGF-$\beta$ increases protein binding to the TGF-$\beta$ element of the pro$\alpha$1(I) collagen gene, whereas corticosteroids reduce protein binding to the TGF-$\beta$ element. It is well known that corticosteroids inhibit wound healing and that TGF-$\beta$ stimulates wound healing. However, treatment of wounds with TGF-$\beta$ results in an overproduction of collagen and subsequent scar formation.

A bimodal therapy involving the use of growth factors together with anti-inflammatory steroids will promote wound healing without the concomitant excessive collagen deposition and subsequent scar formation. Bimodal topical therapy with a pharmaceutical composition comprising an effective amount of a vehicle containing a naturally occurring or synthetic corticosteroid, such as the glucocorticoid dexamethasone, and TGF-$\beta$ together with a pharmaceutically acceptable carrier will reduce the scarring resulting from the treatment of wounds using TGF-$\beta$ alone. This bimodal therapy may be used to enhance normal repair and regeneration of any tissue in any mammal suffering from a wound.

BRIEF DESCRIPTION OF THE DRAWINGS

Cell Culture Data (FIG. 1)

Figure 2:
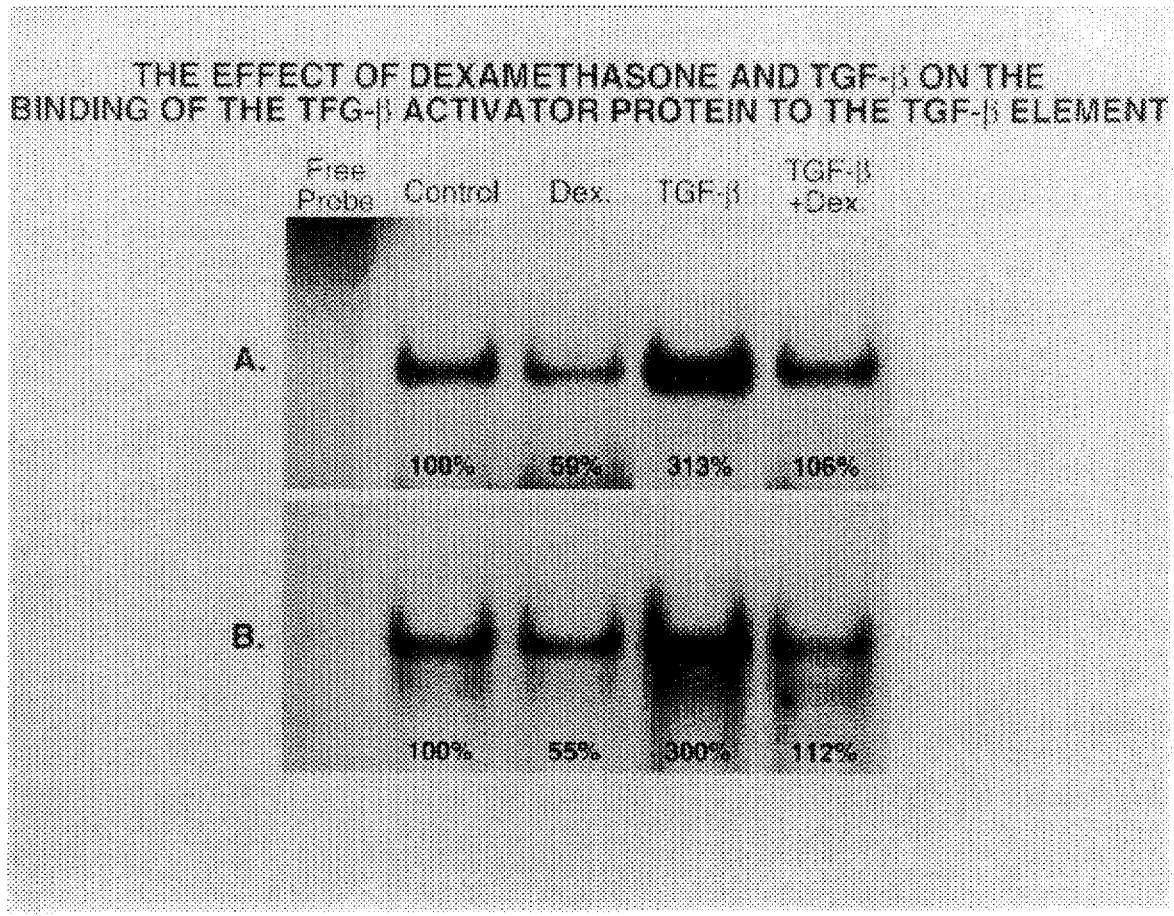

In Vitro Data (FIG. 2)

FIG. 2 represents a gel shift assay that demonstrates the effect of dexamethasone and TGF-$\beta$ on the binding of the TGF-$\beta$ activator protein to the TGF-$\beta$ element. The TGF-$\beta$ activator protein bound to the TGF-$\beta$ element was decreased by dexamethasone treatment and increased by TGF-$\beta$ treatment. Dexamethasone and TGF-$\beta$ co-treatment normalized the TGF-$\beta$ increase of TGF-$\beta$ activator protein bound to the TGF-$\beta$ element to control value.

Figure 3:
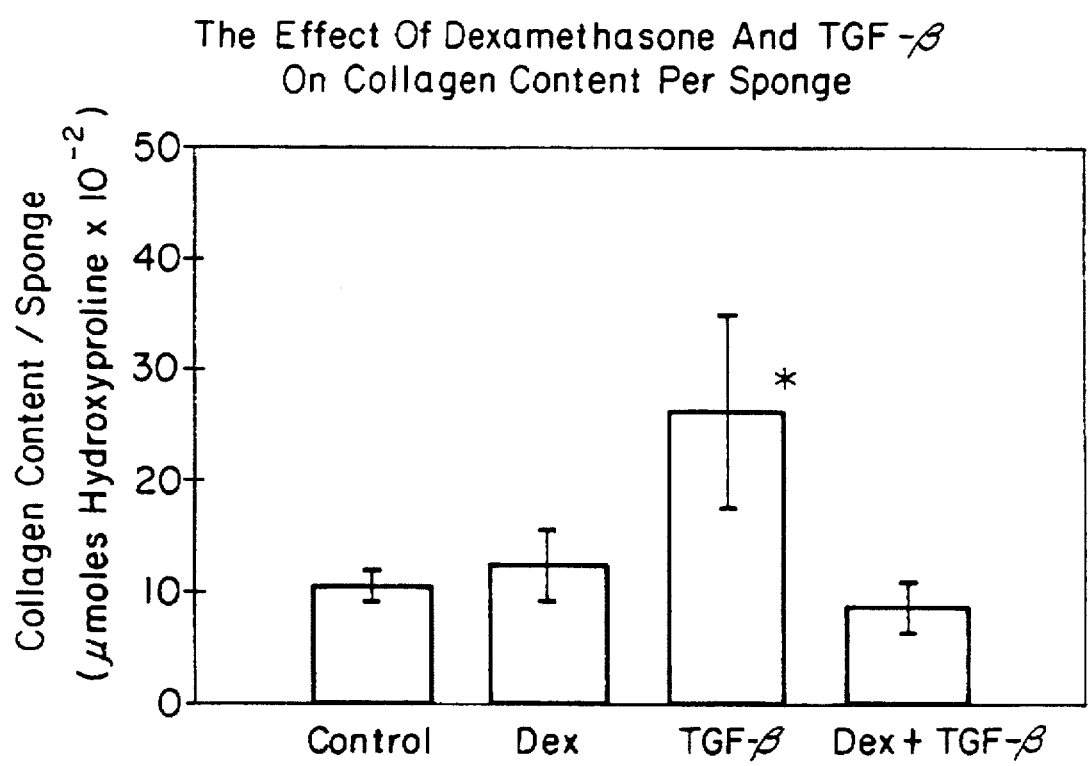

In Vivo Granuloma Model (FIG. 3)

FIG. 3 is a graph that shows the effect of dexamethasone and TGF-$\beta$ co-treatment on the collagen content of each sponge, which is measured as hydroxyproline content. Collagen content was unaffected by dexamethasone treatment but was increased by TGF-$\beta$. Co-treatment with dexamethasone and TGF-$\beta$ normalized the collagen content to control value. The asterisk * signifies a value significantly different from control at P<0.05.

DESCRIPTION OF THE PREFERRED EMBODIMENT

The invention thus relates to a pharmaceutical composition for normalizing the fibrogenic effect of an agonist which comprises an effective amount of an agonist to stimulate collagen synthesis, and an effective amount of an antagonist to reduce the agonist-mediated increase of collagen synthesis and collagen gene expression, together with a pharmaceutically acceptable carrier. Normalization occurs when the amount of collagen synthesized approximates the control value.

A preferred pharmaceutical composition is one in which the agonist is a fibrotic growth factor or a fibrotic growth factor derivative and a particularly preferred pharmaceutical composition is one in which the fibrotic growth factor is TGF-$\beta$.

Another preferred pharmaceutical composition is one in which the agonist activates a signal transduction pathway and a particularly preferred pharmaceutical composition is one in which the agonist activates the serine kinase signal transduction pathway.

Another preferred pharmaceutical composition is one in which the agonist is either a hormone, a vitamin, a vitamin derivative, or a drug. A particularly preferred pharmaceutical composition is one in which the hormone is a naturally occurring or synthetic corticosteroid. A very particularly preferred pharmaceutical composition is one in which the corticosteroid is a glucocorticoid, and a particularly suitable pharmaceutical composition is one in which the glucocorticoid is dexamethasone.

Other preferable pharmaceutical compositions include those in which the vitamin is vitamin A and those in which the vitamin derivative is retinoic acid, both of which are known to regress wound healing.

Another preferred pharmaceutical composition is one in which the carrier is a cream, a gel, an aerosol, a solution, or a powder for topical application.

A further preferred pharmaceutical composition is one incorporated in a patch, a sterile dressing, or an absorbable dressing for topically covering a wound.

Yet another preferred pharmaceutical composition incorporates a biopolymer or a polymer for contacting or implanting into a wound.

The invention also relates to a method of partially blocking or normalizing the fibrogenic effect of an agonist which comprises administering an effective amount of an agonist to stimulate collagen synthesis, and an effective amount of an antagonist to reduce the agonist-mediated increase of collagen synthesis and collagen gene expression, together with a pharmaceutically acceptable carrier.

A preferred method is one in which the agonist is a fibrotic growth factor, and a particularly preferred method is one in which the fibrotic growth factor is TGF-$\beta$.

A further preferred method is one in which the agonist activates a signal transduction pathway, and a particularly preferred method is one in which the pathway is a serine threonine kinase signal transduction pathway.

Another preferred method is one in which the antagonist is either a hormone, a vitamin, a vitamin derivative, or a drug, and a particularly preferred method is one in which the antagonist is a naturally occurring or synthetic corticosteroid. A very particularly preferred method is one in which the corticosteroid is a glucocorticoid, and an especially very particularly preferred method is one in which the glucocortoid is dexamethasone.

Other suitable methods include those in which the vitamin is vitamin A and those in which the vitamin derivative is retinoic acid.

The examples below are intended to illustrate the invention, without in any way limiting it. The references mentioned in the examples are incorporated herein.

EXAMPLES

1. CELL CULTURE DATA

A. Transfection of Rat Skin Fibroblasts

A cell culture of fetal rat skin fibroblasts (RSFs) (American Type Culture Collection, CRL 1213, batch F9707, Rockville, Md.) was stably transfected with the 3.6 ColCat plasmid.[7] Plasmids were purified by double CsCl banding according to standard methods.[8] RSFs were then transfected using the calcium phosphate coprecipitation method.[9] ColCat 3.6 was kindly supplied by D. Rowe and A. Lichtler (Depts. of Pediatrics and Medicine, Univ. Conn. Health Science Center, Farmington, Conn.) and contained the proα1(I) collagen promoter. ColCat 03.6 and pSV2neo were then co-transfected into RSFs for stable cell selection. [10-11] Cells were selected using the neomycin derivative G418 (200 μg/ml).

B. Treatment of Transfected RSF

Stably transfected RSF fibroblasts cultured in synthetic AIM V media (GibcoBRL, Grand Island, N.Y.) were grown to late log phase and treated with either dexamethasone, TGF-$\beta$, or dexamethasone plus TGF-$\beta$. Dexamethasone (Steraloids, Inc., Wilton, N.H.) was added to the fibroblast cultures as a suspension in AIM V media. Dexamethasone was homogenized in media and incubated at 37° C. for 30 min. The suspension was filter-sterilized and diluted to the appropriate concentration prior to addition to the cell cultures so that the final concentration in cell culture was $10^{-6}$M. TGF-$\beta$ obtained from R&D Systems (Minneapolis, Minn.) was added after acid activation to AIM V media at a final concentration of 5 ng/ml. Control cells and cells treated with dexamethasone alone received the vehicle (4 mM HCl with 1 mg/ml bovine serum albumin (Sigma, St. Louis, Mo.) used to dissolve TGF-$\beta$.

C. Preparation of Cell Lysate and Assay of CAT Activity (i.e. Transcription)

At the appropriate time following drug treatment, cells were placed on ice and washed 3× with cold phosphate buffered saline (GibcoBRL, Grand Island, N.Y.). Cells were harvested in 1 ml of 40 mM Tris-HCl, pH 7.4, 150 mM NaCl, and 1 mM EDTA at 4° C. as previously described.[10] The activity of CAT, a reporter gene in place of the proα1(I) gene, was determined.[12] The same amount of protein was added to each reaction mixture containing 100 mM Tris-HCl, pH 7.8 in a volume of 50 μl. Then, 200 μl of 1.25 mM chloramphenicol in 100 mM Tris-HCl, pH 7.8 were added to each sample. Finally, 0.5 μCi [$^3$H]acetyl-CoA (200 mCi/mmol, DuPont NEN, Boston, Mass.) and 22.5 μl of 1 mM unlabeled acetyl-CoA were added and the entire reaction mixture was overlaid with liquid scintillation fluid (Econofluor-2, DuPont NEN, Boston, Mass.). This assay method allowed multiple time points to be determined on the same assay tube by liquid scintillation counting at various times. The acetylated chloramphenicol product was miscible in the aqueous-immiscible scintillation cocktail and the data were collected continuously. Time course activity of each sample was determined and only activity in the linear range of the time course was used. Within each assay, data from the same time point were reported for all samples.

Protein concentration of the cellular lysates was determined.[13]

Figure 1:
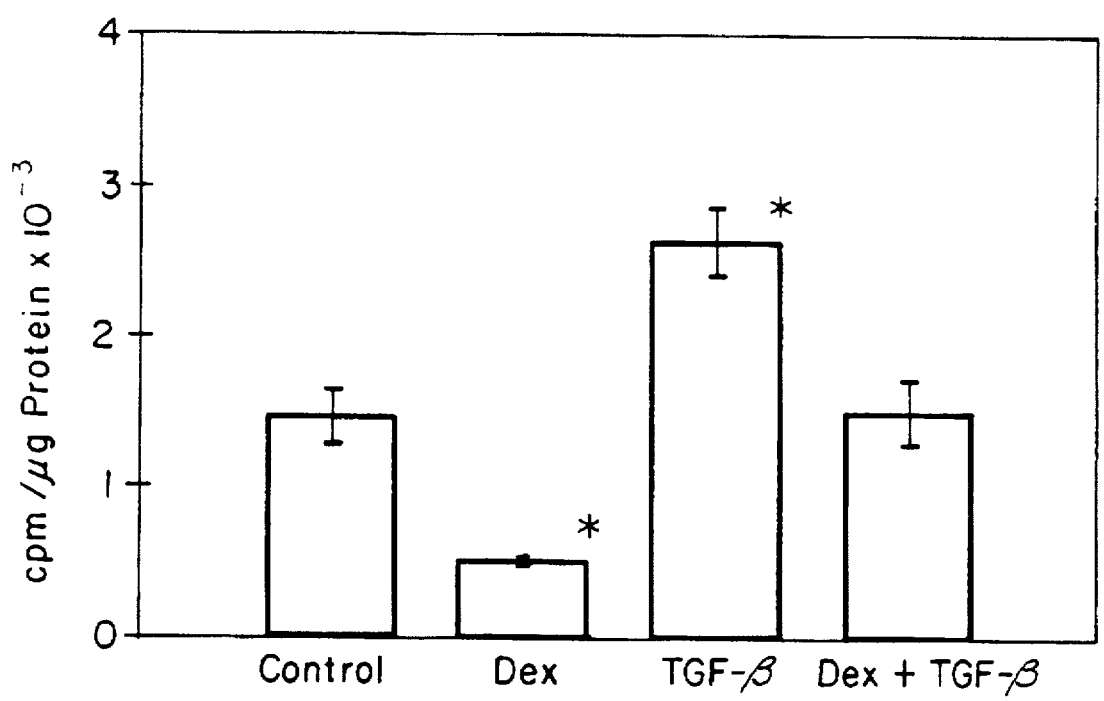
FIG. 1 is a graph that shows the effect of dexamethasone and TGF-$\beta$ co-treatment on chloramphenicol acetyltransferase (CAT) activity. Dexamethasone decreased CAT activity while TGF-$\beta$ increased CAT activity. Dexamethasone and TGF-$\beta$ co-treatment normalized the TGF-$\beta$ increase of CAT activity to control value. The asterisk * indicates a value significantly different from control values at P$\leq$0.01 by student t-Test. Each value represents the mean I.S.D.

D. Cell Culture Data (FIG. 1):

As can be seen in FIG. 1, co-treatment with dexamethasone and TGF-$\beta$ normalized the TGF-$\beta$ mediated stimulation of CAT activity to the control value.

II. IN VITRO DATA: DNA MOBILITY SHIFT ASSAYS

A. Preparation of Nuclear Extracts

RSFs were washed twice with phosphate-buffered saline and placed in AIM V medium for 24 hours. The cells were then treated for 48 hours with either dexamethasone ($10^{-6}$M), TGF-$\beta$ (5 ng/ml), or a mixture of dexamethasone and TGF-$\beta$. Control cells and cells treated with dexamethasone alone received the vehicle (4 mM HCl with 1 mg/ml bovine serum albumin) used to dissolve TGF-$\beta$. After the media was decanted, the cells were washed at 4° C. with physiological saline, scraped with a rubber policeman into centrifuge tubes in a suspension, and collected by centrifugation. Nuclear protein extracts were prepared using a rapid micropreparation technique for extraction of DNA-binding proteins from limiting numbers of mammalian cells [14] and the protein concentration of the cell lysate was determined as previously described.[13]

B. Preparation of the $^{32}$P-oligonucleotide Probe for Mobility Shift Assays

Single-stranded oligonucleotides containing the TGF-$\beta$ element sequence (5-TGC CCACG GCCAG (SEQ ID NO:1)) (SEQ. ID NO:1) were synthesized (Integrated DNA Technologies, Inc., Coralville, Iowa.). In further purification, 20 μg of the single-stranded oligonucleotides were combined with an equal volume of 100% formamide, heated to 90° C. for three minutes and run on a 20% polyacrylamide/8M urea gel in 1×TBE buffer for two hours at 500 V. The DNA was visualized by UV shadowing using ethidium bromide staining. The gel bands containing the DNA were cut from the gel and placed in oligo elution buffer (50 mM Tris-HCl, pH 7.6, 200 mM NaCl, 2 mM EDTA). After overnight incuincubation, the gel particles were removed by centrifugation and the supernatants containing the oligonucleotides were purified on Sep-Pak C28 Cartridges (Millipore Corp., Milford, Mass.). Complementary single-stranded oligonucleotides in 200 mM NaCl were annealed by heating to 95° C. for seven minutes and then slowly cooled to 4° C. The double-stranded oligonucleotides were stored at −20° C.

The double-stranded oligonucleotides were labeled with $^{32}$P-dATP (DuPont NEN, Boston, Mass., 6000 Ci/ummol) using the 5' DNA Terminus Labeling System (GibcoBRL, Grand Island, N.Y.). Gel shift binding reactions (20 μl) contained $^{32}$P-end labeled double-stranded oligonucleotide probes having the TGF-β element sequence (approximately $8\times10^5$ cpM/pM); 10 μg of nuclear protein extract; 1.5 μg of poly d(I-C) (Pharmacia, Piscataway, N.J.); 90 mM KCl; 1 mM EDTA; 1 mM DTT, and 5% glycerol. Reaction mixtures were incubated for 30 minutes at room temperature and separated on a 6% polyacrylamide gel (19:1 acrylamide to bisacrylamide) in 0.25× TBE buffer for four hours at 100 V. The gels were dried and exposed to x-ray film overnight using an intensifying screen. The total radioactivity in each lane (free probe plus TGF-β-activator protein bound to the TGF-β element of the proα1(I) collagen gene) was measured using a densitometer to insure that there was equal loading of each sample onto the gel. The total radioactivity in each lane of each gel did not vary significantly (±6.8%).

C. In Vitro Data (FIG. 2)

The designations at the top of the lanes indicate the treatment regimes of nontransfected RSFs. A and B represent the results from two different experiments carried out under identical conditions, i.e., cell culture treatments, preparation of nuclear extracts, gel conditions for labelling $^{32}$P-oligonucleotide probe, temperatures for annealing and storing of probe. The shaded spots on the gel indicate the binding of the TGF-β activator protein (i.e., the transcription initiation factor) to the TGF-β element found in the 5' flanking region of the proα1(I) collagen gene. As can be seen in FIG. 2, dexamethasone and TGF-β co-treatment normalized the amount of TGF-β activator protein bound to the TGF-β element to approximately control value. Accordingly, the therapeutic advantage of this bimodal therapy would result in the normalization of collagen synthesis by TGF-β and the glucocorticoid, thereby enhancing normal repair and regeneration with reduced scarring in any mammal having a wound or injury repair disorder.

III. IN VIVO GRANULOMA MODEL

A. Surgery on Rats

Male Sprague Dawley rats (Charles River Laboratories, Wilmington, Mass. 250 gm) were acclimated for one week prior to surgery. The rats were divided into four groups: control (n=3); dexamethasone (n=4), (5 μg/sponge); TGF-β (n=3), (50 ng/sponge); and dexamethasone (n=3)(5 μg/sponge) plus TGF-β(50 ng/sponge). Rats weighing approximately 300 gm at the time of surgery were anesthetized with KetasetHCl (AVCCO, Fort-Dodge, Iowa.) (150 mg/rat) and sodium pentobarbital (Abbott Laboratories, North Chicago, Ill.) (100 mg/rat). The abdomen was shaved with an electric razor. A lateral incision was made with scissors. A forceps was inserted under the skin and the facia was separated.

An implant was constructed of a donut polyvinyl alcohol sponge (Unipoint Industries, Inc., High Point, N.C.) with an inner diameter of 5 mm and an outer diameter of 15 mm that was sandwiched between a surgically inert and soft silicone rubber disc that was also 15 mm in diameter (Fisher Scientific, Pittsburgh, Penn.) and a surgically inert and hard polyethylene plastic disc that was 15 mm in diameter (Joshua Meier, North Bergen, N.J.). This implant was held together by skin staples.

B. Treatment of the Sponges

Each implant was injected, while outside the animal, through the soft silicone rubber disc with either 100 μl of 0.9% (w/v) NaCl or 100 μl of 0.9% (w/v) NaCl containing 5 μg of dexamethasone or 50 ng of TGF-β. The dexamethasone plus TGF-β implant was injected with 50 μg of 0.9% (w/v) NaCl containing 5 μg of dexamethasone and 50 μl of 0.9% (w/v) NaCl containing 50 ng of TGF-β. Each implant was located three inches towards the neck region under the skin with the soft silicone rubber disc facing the outer abdomen. The drugs were injected into the lumen of the sponge for five consecutive days with 100 μl of each respective group solution after withdrawing 100 μl of exudate from the lumen of the implant for the next four days after the initial injection.

C. Preparation of Sponges for Hydroxy proline Determination

The rats were sacrificed at the end of the experiment by excess halothane 72 hrs after the last injection and the implant was surgically removed. The skin staples were removed and the silicone rubber and plastic discs were discarded.

The sponge infiltrated with the granulation tissue was hydrolyzed in 1 ml of 6N HCl for 24 hr at 120° C. Activated charcoal Norit A (Fisher Scientific, Fair Lawn, N.J.) was added to each sample and the tubes were centrifuged. A 50 μl sample was used to analyze hydroxyproline, an amino acid found predominately in collagen.[15]

D. In Vivo Granuloma Data (FIG. 3)

The treatment regimes are control (saline), dexamethasone, TGF-β, and dexamethasone plus TGF-β. Each value represents the mean ±S.D. As can be seen in FIG. 3, dexamethasone and TGF-β normalized the amount of collagen (i.e., hydroxyproline per sponge) to control value. The level of dexamethasone was low enough to not affect collagen deposition in the granuloma which would be predicative of what would happen in normal skin tissue surrounding the wound.

Pharmaceutically Acceptable Carrier

Pharmaceutical compositions according to the invention can be incorporated into convenient amounts forms and may employ solid or liquid pharmaceutically acceptable carriers.

Although the dosage and dosage regimen must in each case be carefully adjusted, utilizing sound professional judgment and considering the age, weight, and condition of the recipient, the route of administration, and the nature and gravity of illness, generally the daily dose will be the same ratio of dexamethasone to TGF-β (100:1) used in the granuloma experiment and administered daily. A pharmaceutically acceptable carrier can be a neutral sterile cream, a gel, an aerosol, a solution, or a powder for topical application. The pharmaceutical composition can be incorporated in a patch, a sterile dressing, or an absorbable dressing for topically covering a wound. This composition can also be incorporated in a biopolymer or polymer for contacting or implanting into a wound.

REFERENCES

1. Ritzenthaler et al., Regulation of the α1(I) collagen promoter via a transforming growth factor-β activation element, J. Biol. Chem. 268: 13625–13631 (1993).
2. Jimenez et al., Functional analysis of human α1(I) procollagen gene promoter, J. Biol. Chem. 269: 12684–12691 (1994).
3. Rossi et al., A nuclear factor 1 binding site mediates the transcriptional activation of a type I collagen promoter by transforming growth factor β, Cell 52: 405–414 (1988).
4. Inagaki et al., Transforming growth factor β stimulates α2(I) collagen gene expression through a cis-acting element that contains an Sp1-binding site, J. Biol. Chem. 269: 14828–14834 (1994).
5. Ritzenthaler et al., Transforming-growth-factor-β activation elements in the distal promoter regions of the rat α1 type I collagen gene, Biochem. J. 280: 157–162 (1991).
6. Newman et al., Glucocorticoids selectively decrease the synthesis of hydroxylated collagen peptides, Mol. Pharmacol. 14: 185–198 (1978).
7. Lichtler et al., Isolation and characterization of the rat α(1) collagen promoter, J. Biol. Chem. 264: 3072–3077 (1989).
8. "Current Protocols in Molecular Biology" (Vol. 1, p. 1.7.6).
9. Chen et al., High-efficiency transformation of mammalian cells by plasmid DNA, Mol. Cell Biol. 7: 2745–2752 (1987).
10. Gorman et al., Recombinant genomes which express chloramphenicol acetyltransferase in mammalian cells, Mol. Cell Biol. 2: 1044–1051 (1982).
11. Southern et al., Transformation of mammalian cells to antibiotic resistance with a bacterial gene under control of the SV40 early region promoter, J. Mol. Appl. Genet. 1: 327–341 (1982).
12. Neumann et al., A novel rapid way for chloramphenicol acetyltransferase gene expression, Bio Techniques, 5: 444–447 (1987).
13. Lowry et al., Protein measurement with the folin phenol reagent, J. Biol. Chem. 193: 265–275 (1951).
14. Andrews et al., A rapid micropreparation technique for extraction of DNA-binding proteins from limiting numbers of mammalian cells, Nucleic Acid Res. 19: 2499 (1991).
15. Cutroneo et al., Anti-inflammatory steroids and collagen metabolism: Glucocorticoid-meditated alterations of prolyl hydroxylase activity and collagen synthesis, Mol. Pharmacol. 11: 632–639 (1975).

---

---

What is claimed is:

1. A pharmaceutical composition for bringing the level back to control the fibrogenic effect of a fibrotic growth factor TGFB-1, which acts through the serine threonine kinase signal transduction mechanism and causes scarring, which comprises an effective amount of said growth factor to stimulate collagen synthesis, and an effective amount of an glucocosticoid to reduce the growth factor-mediated increased of collagen synthesis and collagen gene expression, together with a pharmaceutically acceptable carrier in a mammal suffering from a wound or injury repair disorder.

2. The pharmaceutical composition according to claim 1 wherein the glucocorticoid is dexamethasone.

3. The pharmaceutical composition according to claim 1 in which the ratio of the fibrotic growth factor TGFB-1, glucocorticoid is 1:100.

4. The pharmaceutical composition according to claim 1 wherein the carrier is a cream, a gel, an aerosol, a solution, or a powder for topical application.

5. The pharmaceutical composition according to claim 1 incorporated in a patch, a sterile dressing, or an absorbable dressing for topically covering a wound.

6. The pharmaceutical composition according to claim 1 incorporated in a biopolymer or a polymer for contacting or implanting into a wound.

7. A method of normalizing the fibrogenic effect of a fibrotic growth factor which comprises administering to a mammal suffering from a wound or an injury repair disorder an effective amount of the pharmaceutical composition of claim 1.

8. The method according to claim 7 wherein the fibrotic growth factor is TGFB-1.

9. A method according to claim 7 wherein the glucocorticoid is dexamethasone.

* * * * *

UNITED STATES PATENT AND TRADEMARK OFFICE
CERTIFICATE OF CORRECTION

PATENT NO. : 5,798,334

DATED : August 25, 1998

INVENTOR(S) : Kenneth R. Cutroneo

It is certified that error appears in the above-indentified patent and that said Letters Patent is hereby corrected as shown below:

On the title page, in the left hand column, under "References Cited," in the fourth reference cited, "lement" should be -- element --.

column 1, lines 43-44, "inflammatory" should be -- anti-inflammatory --.

column 2, line 65, "agonist" should be -- antagonist --.

column 3, lines 66-67, "synthetic AIM V media (GibcoBRL, Grand Island, N.Y.)" should be -- Dulbecco's modified Eagle's medium (BioWhittaker, Inc., Walkersville, MD) with 5% heat inactivated fetal bovine serum--.

column 4, line 4, "media. Dexamethasone" should be -- media Dexamethasone --. (GibcoBRL, Grand Island, N.Y.).

column 4, line 5, "37° C." should be -- 37° C --.

column 4, line 21, "4° C." should be -- 4° C --.

column 4, line 41, "$^{(13)}$" should be -- $^{(13)}$ --.

column 4, lines 50-51, "($10^-_6$M)" should be -- ($10^{-6}$ M) --.

column 4, line 55, "4° C." should be -- 4° C --.

column 4, line 60, "$(^{14})$" should be -- $^{(14)}$ --.

Column 4, line 63, "$^{32}$P-oligonucleotide" should be --$^{23}$P-Oligonucleotide-- column 4, lines 66-67, "(5-TCG CCACG GCCAG (SEQ ID NO:1)) (SEQ. ID NO:1)" should be -- (5'-TGC CCAG GCCAG) (SEQ. ID NO:1) --.

column 5, line 4, "90° C." should be -- 90° C --.

UNITED STATES PATENT AND TRADEMARK OFFICE
CERTIFICATE OF CORRECTION

PATENT NO. : 5,798,334
DATED : August 25, 1998
INVENTOR(S) : Kenneth R. Cutroneo It is certified that error appears in the above-indentified patent and that said Letters Patent is hereby corrected as shown below:

column 5, line 10, "incuincubation" should be -- incubation --.

column 5, line 11, "supernatants" should be -- supernatant --.

column 5, line 12, "were" should be -- was --.

column 5, line 15, "95° C." should be -- 95° C --.

column 5, line 19, "Ci/ummol" should be -- Ci/mmol --.

column 5, line 24, "cpM/pM" should be -- cpm/pM --.

column 6, line 27, "Hydroxy proline" should be -- Hydroxyproline --.

column 6, line 43, "±S.D." should be -- ±S.E.M. --.

column 6, line 52, "amounts" should be -- amount --.

column 7, line 34, in reference 4, "cis-acting" should be -- *cis*-acting --.

claim 1 at column 8, line 31, "factor TGFB-1," should be -- factor, TGF-$\beta$1, --.

UNITED STATES PATENT AND TRADEMARK OFFICE
CERTIFICATE OF CORRECTION

PATENT NO. : 5,798,334

DATED : August 25, 1998

INVENTOR(S) : Kenneth R. Cutroneo

It is certified that error appears in the above-indentified patent and that said Letters Patent is hereby corrected as shown below:

claim 1 at column 8, line 35, "an glucocosticoid" should be -- a glucocorticoid --.

claim 3 at column 8, line 44, "factor TGFB-1," should be -- factor, TGF-β1, --.

claim 7 at column 8, line 56, "factor which" should be -- factor, TGF-β1, which --.

claim 8 at column 8, line 61, "TGFB-1" should be -- TGF-β1 --.

Signed and Sealed this

Twenty-sixth Day of October, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TGCCCACGGC CAG        13